(12) United States Patent
Xu et al.

(10) Patent No.: US 7,332,636 B2
(45) Date of Patent: Feb. 19, 2008

(54) LOW METAL CONTENT CATALYST COMPOSITIONS AND PROCESSES FOR MAKING AND USING SAME

(75) Inventors: Teng Xu, Houston, TX (US); Stephen Neil Vaughn, Kingwood, TX (US); Richard B. Hall, Whitehouse Station, NJ (US); Kenneth Ray Clem, Humble, TX (US); Jack W. Johnson, Clinton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/581,534

(22) Filed: Oct. 16, 2006

(65) Prior Publication Data

US 2007/0072767 A1    Mar. 29, 2007

Related U.S. Application Data

(62) Division of application No. 10/657,057, filed on Sep. 5, 2003, now Pat. No. 7,125,821.

(51) Int. Cl.
*C07C 1/00* (2006.01)

(52) U.S. Cl. .................. 585/640; 585/638; 585/639

(58) Field of Classification Search ......... 585/638–640
See application file for complete search history.

(56) References Cited

U.S. PATENT DOCUMENTS

| | | | |
|---|---|---|---|
| 3,382,188 A | 5/1968 | Cornelius et al. | |
| 3,433,841 A | 3/1969 | Dehn et al. | |
| 4,089,886 A | 5/1978 | Branecky et al. | |
| 4,556,645 A | 12/1985 | Coughlin et al. | |
| 4,710,485 A | 12/1987 | Miller | |
| 5,379,646 A | 1/1995 | Andrzejak et al. | |
| 5,491,276 A | 2/1996 | O'Young et al. | |
| 5,939,349 A | 8/1999 | Kibby et al. | |
| 6,136,290 A | 10/2000 | Benazzi et al. | |
| 6,137,022 A * | 10/2000 | Kuechler et al. | 585/638 |
| 6,156,290 A | 12/2000 | Lee et al. | |
| 6,290,922 B1 | 9/2001 | Lee et al. | |
| 6,440,894 B1 | 8/2002 | Martens et al. | |
| 6,464,857 B2 | 10/2002 | Miller | |
| 6,472,441 B1 | 10/2002 | Kibby | |
| 6,475,463 B1 | 11/2002 | Elomari et al. | |
| 6,509,290 B1 | 1/2003 | Vaughn et al. | |
| 6,660,682 B2 | 12/2003 | Cao et al. | |
| 6,737,556 B2 | 5/2004 | Jones et al. | |
| 6,787,501 B2 | 9/2004 | Vaughn et al. | |
| 7,034,196 B2 | 4/2006 | Clem et al. | |
| 7,160,831 B2 | 1/2007 | Vaughn et al. | |
| 2002/0016522 A1 | 2/2002 | Vaughn et al. | |
| 2002/0055433 A1 | 5/2002 | Fung et al. | |
| 2003/0018228 A1 | 1/2003 | Martens et al. | |
| 2004/0034264 A1 | 2/2004 | Janssen et al. | |

FOREIGN PATENT DOCUMENTS

| | | |
|---|---|---|
| EP | 175 799 | 2/1986 |
| EP | 951 444 | 7/2001 |
| EP | 1 054 050 | 5/2003 |
| FR | 2 662 704 | 6/1990 |
| WO | WO 99/21651 | 5/1999 |
| WO | WO 02/05952 | 1/2002 |
| WO | WO 02/26380 | 4/2002 |
| WO | WO 03/000412 | 3/2003 |
| WO | WO 03/000413 | 3/2003 |

OTHER PUBLICATIONS

Zafir Ekmekei et al., "Desulphurisation of Ivrindi Alunitic Kaolin," Yerbilimleri, 23 (2001) pp. 53-60, retrieved May 3, 2001.
Frank Hart, "Work well-advanced at 7 million-plus development of UK kaolin production complex," International Ceramics, Issue 1, 2000, retrieved May 3, 2001.
Ahmet R. Mermut et al., "Baseline Studies of the Clay Minerals Society Source Clays: Chemical Analyses of Major Elements," Clays and Clay Minerals, vol. 49, No. 5, pp. 381-386 (2001), retrieved May 3, 2001.
William F. Moll, Jr., "Baseline Studies of the Clay Minerals Society Source Clays: Geological Origin," Clays and Clay Minerals, vol. 49, No. 5, pp. 374-380 (2001), retrieved May 3, 2001.
"Types of Clays", Ceramics Today. http://www.ceramicstoday.com/articles/042301a.htm, 1 page, retrieved on May 3, 2001.
"What is Kaolin?" http://www.ima-eu.org/cn/ckawhat.html, pp. 1-9, retrieved on May 3, 2001.
"Kaolin" http://www.miningtrading.com/more/kaolin/, p. 1-2, retrieved on May 3, 2001.
"Raw Clays" http://www.claymaker.com/ceramic_central/info/raw_clays.htm, pp. 1-5, retrieved on May 3, 2001.

* cited by examiner

*Primary Examiner*—Glenn Caldarola
*Assistant Examiner*—In Suk Bullock

(57) ABSTRACT

The invention provides low metal content molecular sieve catalyst compositions, processes for making such catalysts, and processes for using such catalysts in the conversion of an oxygenate into one or more light olefins. Preferably, the catalyst composition comprises a matrix material having a low metal content. By utilizing matrix materials having low metal contents, the amount of metal-catalyzed side reaction byproducts formed in a reaction system, particularly in an oxygenate-to-olefin reaction system, can be advantageously reduced.

23 Claims, No Drawings

LOW METAL CONTENT CATALYST COMPOSITIONS AND PROCESSES FOR MAKING AND USING SAME

This application is a divisional of U.S. patent application Ser. No. 10/657,057, filed Sep. 5, 2003, now U.S. Pat. No. 7,125,821 and is fully incorporated herein by reference.

FIELD OF THE INVENTION

The present invention relates to a molecular sieve catalyst composition formed, in part, of a matrix material having a low metal content, to a process of forming the molecular sieve catalyst composition, and to conversion processes using the molecular sieve catalyst composition.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in a variety of processes for making plastics and other chemical compounds.

The petrochemical industry has known for some time that oxygenates, particularly alcohols, are convertible in the presence of molecular sieve catalysts into light olefins. Molecular sieves are porous solids having pores of different sizes such as zeolites or zeolite-type molecular sieves, carbons and oxides. The most commercially useful molecular sieves for the petroleum and petrochemical industries are known as zeolites, for example aluminosilicate molecular sieves. Zeolites in general have a one-, two- or three-dimensional crystalline pore structure having uniformly sized pores of molecular dimensions that selectively adsorb molecules that can enter the pores, and exclude those molecules that are too large.

Typically, molecular sieves are formed into molecular sieve catalyst compositions to improve their durability, control reactivity and improve cost-effectiveness in commercial conversion processes. Molecular sieve catalyst compositions are formed by combining a molecular sieve and a matrix material usually in the presence of a binder. Matrix materials, such as clays, are typically effective in reducing overall catalyst cost, acting as thermal sinks to assist in shielding heat from the catalyst composition for example during regeneration, densifying the catalyst composition, increasing catalyst strength such as crush strength and attrition resistance, and in controlling the rate of conversion in a particular process. The purpose of the binder is hold the matrix material to the molecular sieve.

In a typical MTO reaction system, undesirable byproducts may be formed through side reactions. For example, metals forming conventional reactor walls may act as catalysts in one or more side reactions. If the methanol feedstock contacts the metal reactor wall at sufficient temperature and pressure, the methanol may be converted to undesirable methane and/or other byproducts. Additionally, ethylene and propylene may react with steam at elevated temperatures and in the presence of certain metals to undesirably form acetaldehyde and acetone byproducts.

Byproduct formation in an MTO reactor is undesirable for several reasons. First, increased investment is required to separate and recover the byproducts from the desired light olefins. Additionally, as more byproducts are formed, less light olefins are synthesized. That is, the production of byproducts is undesirable because methanol feed is consumed to produce the byproducts. Further, although the relative concentrations of metal catalyzed side reaction byproducts are generally quite low, the total amount of byproducts produced on an industrial scale can be enormous. Thus, it is desirable to decrease or eliminate the synthesis of byproducts in an MTO reaction system.

Pending U.S. patent application Ser. No. 10/175,285, which was filed on Jun. 19, 2002, the entirety of which is incorporated herein by reference, discloses a method and apparatus for reducing the amount of metal catalyzed side-reaction byproducts formed in the feed vaporization and introduction ("FVI") system of an MTO reaction system. In an FVI system of a reaction system, the feedstock is at least partially vaporized by one or more heating devices, is passed through feed lines to a feed introduction nozzle or nozzles, and is introduced into the reactor. Specifically, according to the '285 application, the temperature of at least a portion of the FVI system and/or of the feedstock contained therein is monitored and/or maintained below about 400° C. The temperature can be maintained in the desired range by jacketing at least a portion of the FVI system, such as at least a portion of the feed introduction nozzle, with a thermally insulating material or by implementing a cooling system.

Pending U.S. patent application Ser. No. 10/274,739, filed Oct. 21, 2002, the entirety of which is incorporated herein by reference, also is directed to reducing the formation of metal catalyzed side-reaction byproducts in the FVI system. Specifically, the '739 application discloses a method and system for reducing the formation of metal catalyzed side-reaction byproducts formed in the FVI system of an MTO reaction system by forming and/or coating one of more heating devices, feed lines or feed introduction nozzles of/with a material that is resistant to the formation of metal catalyst side reaction byproducts.

It has now been discovered that the presence of certain metals in the matrix material of a molecular sieve catalyst composition may exacerbate the formation of metal catalyzed side-reaction byproducts in an MTO reaction system. Thus, a need exists for reducing the formation of metal catalyzed side-reaction byproducts in an MTO reaction system caused by matrix materials in molecular sieve catalyst compositions.

SUMMARY OF THE INVENTION

This invention provides a molecular sieve catalyst composition formed of a matrix material having a low metal content, processes for making such catalysts, and processes for using such catalysts in the conversion of an oxygenate-containing feedstock into one or more light olefins. The molecular sieve catalyst composition is formed from the combination of a molecular sieve, a matrix material and optionally a binder. According to the present invention, the selected matrix material has a low metal content. By forming catalyst compositions from matrix materials having low metal contents, the amount of metal-catalyzed side reaction byproducts formed in a reaction system, particularly in a methanol-to-olefin reaction system, can be advantageously reduced.

In one embodiment, the invention is directed to a catalyst composition including a molecular sieve, a matrix material containing less than about 10,000 wppm iron and iron-containing species, based on the total weight of the matrix material, and optionally binder. Optionally, the matrix material contains less than about 7,000 wppm, or less than 4,000 wppm iron and iron-containing species, based on the total weight of the matrix material. The matrix material optionally is selected from the group consisting of: kaolin, halloysite, kaolinite, dickite, nacrite, hectorite and laponite. The catalyst composition preferably has a d50 particle size from about 20 to about 200 microns. The molecular sieve preferably is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof and mixtures thereof. Optionally, the catalyst composition is a slurry and the catalyst composition further comprises a slurrying medium.

In another embodiment, the invention is directed to a catalyst composition including a molecular sieve, a matrix material containing less than about 15,000 wppm titanium and titanium-containing species, based on the total weight of the matrix material, and optionally binder. Optionally, the matrix material contains less than about 10,000 wppm or less than about 5,000 wppm titanium and titanium-containing species, based on the total weight of the matrix material. The matrix material optionally is selected from the group consisting of: kaolin, halloysite, kaolinite, dickite, nacrite, montmorillonite, saponite, hectorite and laponite. The catalyst composition preferably has a d50 particle size from about 20 to about 200 microns. The molecular sieve preferably is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof and mixtures thereof. Optionally, the catalyst composition is a slurry and the catalyst composition further comprises a slurrying medium.

In another embodiment, the invention is directed to a catalyst composition including a molecular sieve, a matrix material containing less than about 1,500 wppm nickel and nickel-containing species, based on the total weight of the matrix material, and optionally binder. Optionally, the matrix material contains less than about 300 wppm or less than about 150 wppm nickel and nickel-containing species, based on the total weight of the matrix material. The matrix material optionally is selected from the group consisting of: kaolin, halloysite, kaolinite, dickite, nacrite, montmorillonite, hectorite, saponite and laponite. The catalyst composition preferably has a d50 particle size from about 20 to about 200 microns. The molecular sieve preferably is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof and mixtures thereof. Optionally, the catalyst composition is a slurry and the catalyst composition further comprises a slurrying medium.

In another embodiment, the invention is directed to a catalyst composition including a molecular sieve, a matrix material containing less than about 1,500 wppm manganese and manganese-containing species, based on the total weight of the matrix material, and optionally binder. Optionally, the matrix material contains less than about 300 wppm or less than about 150 wppm manganese and manganese-containing species, based on the total weight of the matrix material. The matrix material optionally is selected from the group consisting of: kaolin, halloysite, kaolinite, dickite, nacrite, montmorillonite, hectorite, saponite and laponite. The catalyst composition preferably has a d50 particle size from about 20 to about 200 microns. The molecular sieve preferably is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof and mixtures thereof. Optionally, the catalyst composition is a slurry and the catalyst composition further comprises a slurrying medium.

In another embodiment, the invention is directed to a catalyst composition including a molecular sieve, a matrix material containing less than about 1,500 wppm vanadium and vanadium-containing species, based on the total weight of the matrix material, and optionally binder. Optionally, the matrix material contains less than about 300 wppm or less than about 150 wppm vanadium and vanadium-containing species, based on the total weight of the matrix material. The matrix material optionally is selected from the group consisting of: kaolin, halloysite, kaolinite, dickite, nacrite, montmorillonite, hectorite, saponite and laponite. The catalyst composition preferably has a d50 particle size from about 20 to about 200 microns. The molecular sieve preferably is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof and mixtures thereof. Optionally, the catalyst composition is a slurry and the catalyst composition further comprises a slurrying medium.

In another embodiment, the invention is directed to a catalyst composition including a molecular sieve, a matrix material containing less than about less than about 1,500 wppm cobalt and cobalt-containing species, based on the total weight of the matrix material, and optionally binder. Optionally, the matrix material contains less than about 100 wppm or less than about 5 wppm cobalt and cobalt-containing species, based on the total weight of the matrix material. The matrix material optionally is selected from the group consisting of: kaolin, halloysite, kaolinite, dickite, nacrite, montmorillonite, hectorite, saponite and laponite. The catalyst composition preferably has a d50 particle size from about 20 to about 200 microns. The molecular sieve preferably is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, the metal containing forms thereof, intergrown forms thereof and mixtures thereof. Optionally, the catalyst composition is a slurry and the catalyst composition further comprises a slurrying medium.

The invention is also directed to a process for forming a molecular sieve catalyst composition. The process includes selecting a matrix material containing less than 10,000 wppm of iron and iron-containing species, based on the total weight of the matrix material. A slurry is formed containing the matrix material, molecular sieves, optionally a binder, and a slurrying medium. The slurry is dried to produce the molecular sieve catalyst composition. Optionally, the selected matrix material contains less than about 7,000 wppm, or less than 4,000 wppm iron and iron-containing species, based on the total weight of the matrix material.

In another embodiment, the invention includes selecting a matrix material containing less than 15,000 wppm of titanium and titanium-containing species, based on the total weight of the matrix material. A slurry is formed containing the matrix material, molecular sieves, optionally a binder, and a slurrying medium. The slurry is dried to produce the molecular sieve catalyst composition. Optionally, the matrix material contains less than about 10,000 wppm or less than about 5,000 wppm titanium and titanium-containing species, based on the total weight of the matrix material.

In another embodiment, the invention includes selecting a matrix material containing less than 1,500 wppm of nickel and nickel-containing species, based on the total weight of the matrix material. A slurry is formed containing the matrix material, molecular sieves, optionally a binder, and a slurrying medium. The slurry is dried to produce the molecular sieve catalyst composition. Optionally, the matrix material contains less than about 300 wppm or less than about 150 wppm nickel and nickel-containing species, based on the total weight of the matrix material.

In another embodiment, the invention includes selecting a matrix material containing less than 1,500 wppm of manganese and manganese-containing species, based on the total weight of the matrix material. A slurry is formed containing the matrix material, molecular sieves, optionally a binder, and a slurrying medium. The slurry is dried to produce the molecular sieve catalyst composition. Optionally, the matrix material contains less than about 300 wppm or less than about 150 wppm manganese and manganese-containing species, based on the total weight of the matrix material.

In another embodiment, the invention includes selecting a matrix material containing less than 1,500 wppm of vanadium and vanadium-containing species, based on the total weight of the matrix material. A slurry is formed containing the matrix material, molecular sieves, optionally a binder, and a slurrying medium. The slurry is dried to produce the molecular sieve catalyst composition. Optionally, the matrix material contains less than about 300 wppm or less than about 150 wppm vanadium and vanadium-containing species, based on the total weight of the matrix material.

In another embodiment, the invention includes selecting a matrix material containing less than 1,500 wppm of cobalt and cobalt-containing species, based on the total weight of the matrix material. A slurry is formed containing the matrix material, molecular sieves, optionally a binder, and a slurrying medium. The slurry is dried to produce the molecular sieve catalyst composition. Optionally, the matrix material contains less than about 100 wppm or less than about 5 wppm cobalt and cobalt-containing species, based on the total weight of the matrix material.

In another embodiment, the invention is directed to a catalyst composition including a molecular sieve, a matrix material, and optionally a binder. The catalyst composition contains less than about 10,000 wppm iron and iron-containing species, based on the total weight of the catalyst composition. Optionally, the catalyst composition contains less than about 7,000 wppm or less than about 4,000 wppm iron and iron-containing species, based on the total weight of the catalyst composition.

In another embodiment, the invention is directed to a catalyst composition including a molecular sieve, a matrix material, and optionally a binder. The catalyst composition contains less than about 15,000 wppm titanium and titanium-containing species, based on the total weight of the catalyst composition. Optionally, the catalyst composition contains less than about 10,000 wppm or less than about 5,000 wppm titanium and titanium-containing species, based on the total weight of the catalyst composition.

In another embodiment, the invention is directed to a catalyst composition including a molecular sieve, a matrix material, and optionally binder. The catalyst composition contains less than about 1,500 wppm nickel and nickel-containing species, based on the total weight of the catalyst composition. Optionally, the catalyst composition contains less than about 300 wppm or less than about 150 wppm nickel and nickel-containing species, based on the total weight of the catalyst composition.

In another embodiment, the invention is directed to a catalyst composition including a molecular sieve, a matrix material, and optionally binder. The catalyst composition contains less than about 1,500 wppm cobalt and cobalt-containing species, based on the total weight of the catalyst composition. Optionally, the catalyst composition contains less than about 100 wppm or less than about 5 wppm cobalt and cobalt-containing species, based on the total weight of the catalyst composition.

In another embodiment, the invention is directed to a catalyst composition including a molecular sieve, a matrix material, and optionally binder. The catalyst composition contains less than about 1,500 wppm manganese and manganese-containing species, based on the total weight of the catalyst composition. Optionally, the catalyst composition contains less than about 300 wppm or less than about 150 wppm manganese and manganese-containing species, based on the total weight of the catalyst composition.

In another embodiment, the invention is directed to a catalyst composition including a molecular sieve, a matrix material, and optionally binder. The catalyst composition contains less than about 1,500 wppm vanadium and vanadium-containing species, based on the total weight of the catalyst composition. Optionally, the catalyst composition contains less than about 300 wppm or less than about 150 wppm vanadium and vanadium-containing species, based on the total weight of the catalyst composition.

By implementing a low-metal content catalyst composition in an oxygenate-to-olefin reaction system, the amount of metal-catalyzed side reaction byproducts formed in the oxygenate-to-olefin reaction system can be advantageously reduced. Thus, in one embodiment, the invention is directed to a process for producing light olefins. The process includes providing an oxygenate in an oxygenate-containing feedstock. The oxygenate contacts a molecular sieve catalyst composition under conditions effective to convert at least a portion of the oxygenate to light olefins and oxygenate byproducts in a reaction effluent. The reaction effluent contains less than about 10 weight percent oxygenate byproducts, based on the total weight of the reaction effluent. Depending on the metal content in the catalyst composition, the reaction effluent optionally contains less than about 5 weight percent, less than about 3 weight percent, or less than about 1 weight percent oxygenate byproducts, based on the total weight of the reaction effluent.

DETAILED DESCRIPTION OF THE INVENTION

I. Introduction

The present invention is directed to reducing or eliminating the formation of metal catalyzed side reaction byproducts in a reaction system, and in particular, in an oxygenate to olefin (OTO) reaction system such as a methanol to olefin (MTO) reaction system. When a feedstock containing an oxygenate such as methanol contacts a metal-containing surface or particle, e.g., a catalyst composition formed of a metal-containing matrix material, at relatively high temperatures and pressures, the oxygenate in the feedstock decomposes to form undesirable byproducts. Additionally, light olefins such as ethylene and propylene may undesirably react with steam to form acetaldehyde and acetone. The invention is directed toward a molecular sieve catalyst composition, its making, and to its use in the conversion of an oxygenate-containing feedstock into one or more olefins. The molecular sieve catalyst composition is made or formed from the combination of a molecular sieve, a matrix material and optionally a binder. According to the present invention, the matrix material selected has a low metal content. By providing a matrix material having a low metal content, the amount of metal catalyzed side reaction byproducts formed in an OTO reaction system can be advantageously reduced.

II. Metal-Catalyzed Side Reactions in OTO Reaction Systems

It has now been discovered that in addition to metal catalyzed side reactions occurring on reactor walls and in FVI systems, the metal in one or more catalyst compositions may undesirably catalyze the conversion of an oxygenate such as methanol to one or more metal-catalyzed side reaction byproducts, particularly in an OTO reaction system. Conventional matrix materials used in forming catalyst compositions contain particularly high metal levels. In one embodiment of the present invention, a catalyst composition is formed, preferably for use in an OTO reaction system, which catalyst composition contains a matrix material having a low metal content. The catalyst compositions formed according to the present invention are capable of reducing the formation of metal catalyzed side reaction byproducts. By reducing the formation of metal catalyzed side reaction byproducts, the time and costs associated with separating these byproducts from the desired product can be reduced or eliminated resulting in a significant commercial savings.

As an oxygenate-containing feedstock contacts a conventional catalyst composition, particularly in an MTO reaction system, the oxygenate in the feedstock contacts one or more metals in the matrix material of the conventional catalyst composition and undergoes one or more side reactions. The metals in the matrix material of conventional catalyst compositions are believed to act as catalysts at high temperatures and pressures that facilitate conversion of some of the oxygenate in the feedstock to hydrogen, carbon monoxide, carbon dioxide, methane and/or graphite. Iron and several other metals, such as nickel, platinum, titanium, cobalt, manganese, vanadium and palladium, are particularly active for catalyzing methanol decomposition at high temperatures. Chromium is mildly active for catalyzing the formation of side-reaction byproducts from an oxygenate-containing feedstock.

Without limiting the invention to a particular reaction mechanism to be avoided, if the oxygenate is methanol, the side reaction may be illustrated as follows:

(I)

In conventional MTO reaction systems, the temperature within the MTO reactor is generally much higher than the minimum temperatures that are conducive to the formation of metal catalyzed side reaction byproducts. Ideally, the MTO reactor is a fluidized bed reactor, wherein the catalyst composition contained therein is in a fluidized state. As a result, heat from the MTO reactor is readily transferred to the fluidized catalyst compositions contained therein.

Further, as the feedstock contacts the conventional metal-containing catalyst compositions at high weight hourly space velocities (WHSV) and under extreme temperature and pressure conditions, a portion of the catalyst compositions can shear or break away, e.g., attrite to form one or more smaller catalyst attrition particles, thereby increasing the metal surface area in the reaction system. This increased metal surface area in the reaction system further facilitates the formation of metal catalyzed side reaction byproducts. Catalyst attrition can also produce an undesirable mixture of powdery carbon and metal particles, which can become entrained with the product light olefins and must be removed therefrom, e.g., by centrifugation or filtering.

Catalyst attrition has negatively impacted the efficiency and productivity of processes within numerous industries. In MTO reaction systems, catalyst attrition facilitates the formation of metal catalyzed side reaction byproducts because the ratio of metal surface area to volume of feedstock increases as catalyst attrition occurs. In accordance with the present invention, metal dusting is not as significant of a problem as in conventional reaction systems, because although catalyst compositions may still attrite, the resulting catalyst attrition particles have a low metal content because the matrix materials selected to form the catalyst compositions have a low metal content. Thus, the present invention has an additional advantage in that catalyst attrition will not significantly increase the formation of metal-catalyzed side reaction byproducts.

In addition, the light olefin products ethylene and propylene react with steam at high temperatures and in the presence of certain metals to undesirably form acetaldehyde and acetone, respectively. The equilibrium reactions for these conversions may be illustrated as shown by reactions (II) and (III), below.

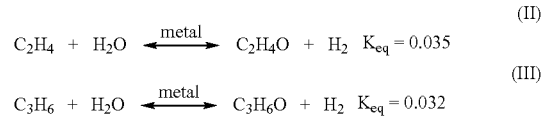

An MTO reaction system operating at or close to 100 percent conversion forms a reaction effluent containing about 56 weight percent water, 13 weight percent ethylene, 18 weight percent propylene, and 7 weight percent butenes. When using high metal content catalyst compositions in an MTO reaction system, the relatively high water, ethylene and propylene concentrations formed in an MTO reaction effluent, exacerbated by the high reaction temperatures necessary to convert methanol to olefins, undesirably favors the conversion of ethylene to acetaldehyde, and propylene to acetone. The magnitudes of the equilibrium constants for olefin hydration followed by oxidation suggest that an appreciable amount of acetone and acetaldehyde byproducts will be produced in an MTO reaction system that utilizes high metal content catalyst compositions. Since oxidation reactions are catalyzed by metals, such as $Fe^{3+}$, mitigation or elimination of the formation of these undesirable oxygenates can be realized by forming and utilizing catalyst compositions having low metal contents.

III. Molecular Sieves and Catalysts Thereof

Molecular sieves have various chemical, physical, and framework characteristics. Molecular sieves have been well classified by the Structure Commission of the International Zeolite Association according to the rules of the IUPAC Commission on Zeolite Nomenclature. A molecular sieve's "framework-type" describes the connectivity and topology of the tetrahedrally coordinated atoms constituting the framework, and makes an abstraction of the specific properties for those materials. Framework-type zeolite and zeolite-type molecular sieves for which a structure has been established are assigned a three letter code and are described in the Atlas of Zeolite Framework Types, 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI framework-type or a CHA framework-type, or a combination thereof, most preferably a CHA framework-type.

Molecular sieve materials all have 3-dimensional framework structure of corner-sharing TO4 tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pages 1-67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing [TO4] tetrahedral units, more preferably, two or more [SiO4], [AlO4] and/or [PO4] tetrahedral units, and most preferably [SiO4], [AlO4] and [PO4] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. Nos. 4,973,460 (LiAPSO), 4,789,535 (LiAPO), 4,992,250 (GeAPSO), 4,888,167 (GeAPO), 5,057,295 (BAPSO), 4,738,837 (CrAPSO), 4,759,919, and 4,851,106 (CrAPO), U.S. Pat. Nos. 4,758,419, 4,882,038, 5,434,326 and 5,478,787 (MgAPSO), 4,554,143 (FeAPO), 4,894,213 (AsAPSO), 4,913,888 (AsAPO), 4,686,092, 4,846,956 and 4,793,833 (MnAPSO), 5,345,011 and 6,156,931 (MnAPO), 4,737,353 (BeAPSO), 4,940,570 (BeAPO), 4,801,309, 4,684,617 and 4,880,520 (TiAPSO), 4,500,651, 4,551,236 and 4,605,492 (TiAPO), 4,824,554, 4,744,970 (CoAPSO), 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are fully incorporated herein by reference. Other molecular sieves are described in R. Szostak, Handbook of Molecular Sieves, Van Nostrand Reinhold, New York, N.Y. (1992), which is fully incorporated herein by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO2], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of M, Al and P as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. Preferably, the molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof. Optionally, the molecular sieve is selected from the group consisting of SAPO-34, the metal containing forms thereof, and mixtures thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the molar ratio of CHA to AEI is greater than 1:1.

IV. Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline molecular sieve material is formed, and then recovered by filtration, centrifugation and/or decanting.

In a preferred embodiment, the molecular sieves are synthesized by forming a reaction product of a source of silicon, a source of aluminum, a source of phosphorous, and/or an organic templating agent, preferably a nitrogen containing organic templating agent. This particularly preferred embodiment results in the synthesis of a silicoaluminophosphate crystalline material that is then isolated by filtration, centrifugation and/or decanting.

Non-limiting examples of silicon sources include silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as ALPO4, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula R4N+, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, polyethylenimine and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source.

A synthesis mixture containing at a minimum a silicon-, aluminum-, and/or phosphorous-composition, and a templating agent, should have a pH in the range of from 2 to 10, preferably in the range of from 4 to 9, and most preferably in the range of from 5 to 8. Generally, the synthesis mixture is sealed in a vessel and heated, preferably under autogenous pressure, to a temperature in the range of from about 80° C. to about 250° C., and more preferably from about 150° C. to about 180° C. The time required to form the crystalline product is typically from immediately up to several weeks, the duration of which is usually dependent on the temperature; the higher the temperature the shorter the duration. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

Molecular sieves have either a high silicon (Si) to aluminum (Al) atomic ratio or a low silicon to aluminum atomic ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

V. Low Metal Content Matrix Materials and Catalyst Compositions

Once the molecular sieve is synthesized as described above, depending on the requirements of the particular conversion process, the molecular sieve is then formulated into a molecular sieve catalyst composition as described in more detail below. The molecular sieves synthesized above are made or formulated into molecular sieve catalyst compositions by combining the synthesized molecular sieve(s) with one or more matrix materials and optionally a binder to form a formulation composition.

Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, non-active, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron, cobalt, nickel, titanium, palladium, chromium and/or platinum content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a d90 particle size distribution of less than about 1 µm.

In one embodiment of the present invention, the selected matrix material contains less than about 10,000 wppm, more preferably less than about 7,000 wppm, and most preferably less than about 4,000 wppm iron and iron-containing species, based on the total weight of the matrix material. Unless otherwise stated, any reference herein to the amount of a metal and metal-containing species in a matrix material, e.g., "less than about 4,000 wppm iron and iron-containing species," means that the matrix material contains less than the stated amount of metal and metal-containing species, collectively. That is, the combined content of the metal and any metal-containing species in the matrix material is less than the stated value.

Preferably, the low iron content matrix material is selected from the group consisting of: kaolin, halloysite, kaolinite, dickite, nacrite, hectorite and laponite. However, Smectites such as laponite and hectorite are less preferred matrix materials because they tend to form highly viscous slurries, which do not atomize well during spray-drying. Typically, these exemplary low iron content matrix materials have varying iron content levels, depending on the particular matrix material sample. For example, one kaolin clay from one sample may have a higher iron content than a kaolin clay from another sample, e.g., obtained from another region. As a result, to ensure that a particular clay sample contains a sufficiently low iron content and is suitable as a matrix material, the clay sample preferably is analyzed through well-known techniques, e.g., through inductively coupled plasma atomic emission spectroscopy (ICP/AES), atomic adsorption spectroscopy (AAS) and/or x-ray fluorescence (XRF) to determine whether the clay sample's iron content is below any of the above-provided predetermined iron content limits.

In another embodiment of the present invention, the selected matrix material comprises less than about 15,000 wppm, more preferably less than about 10,000 wppm, and most preferably less than about 5,000 wppm titanium and titanium-containing species, based on the total weight of the matrix material. Preferably, the low titanium content matrix material is selected from the group consisting of: kaolin, halloysite, kaolinite, dickite, nacrite, montmorillonite, saponite, hectorite and laponite. Typically, these exemplary low titanium content matrix materials have varying titanium content levels, depending on the particular matrix material sample. For example, one kaolin clay from one sample may have a higher titanium content than a kaolin clay from another sample, e.g., obtained from another region. As a result, to ensure that a particular clay sample contains a sufficiently low titanium content to be suitable as a matrix material, the clay sample preferably is analyzed through well-known techniques, described in more detail below, to determine whether the clay sample's titanium content is below any of the above-provided predetermined titanium content limits.

In another embodiment of the present invention, the selected matrix material comprises less than about 1,500 wppm, more preferably less than about 300 wppm, and most preferably less than about 150 wppm nickel and nickel-containing species, based on the total weight of the matrix material. Preferably, the low nickel content matrix material is selected from the group consisting of: kaolin, halloysite, kaolinite, dickite, nacrite, montmorillonite, hectorite, saponite and laponite. Typically, these exemplary low nickel content matrix materials have varying nickel content levels, depending on the particular matrix material sample. For example, one kaolin clay from one sample may have a higher nickel content than a kaolin clay from another sample, e.g., obtained from another region. As a result, to ensure that a particular clay sample contains a sufficiently low nickel content to be suitable as a matrix material, the clay sample preferably is analyzed through well-known techniques, described in more detail below, to determine whether the clay sample's nickel content is below any of the above-provided predetermined nickel content limits.

In another embodiment of the present invention, the selected matrix material comprises less than about 1,500 wppm, more preferably less than about 300 wppm, and most preferably less than about 150 wppm manganese and manganese-containing species, based on the total weight of the matrix material. Preferably, the low manganese content matrix material is selected from the group consisting of: kaolin, halloysite, kaolinite, dickite, nacrite, montmorillonite, hectorite, saponite and laponite. Typically, these exemplary low nickel content matrix materials have varying manganese content levels, depending on the particular matrix material sample. For example, one kaolin clay from one sample may have a higher manganese content than a kaolin clay from another sample, e.g., obtained from another region. As a result, to ensure that a particular clay sample contains a sufficiently low manganese content to be suitable as a matrix material, the clay sample preferably is analyzed through well-known techniques, described in more detail below, to determine whether the clay sample's manganese content is below any of the above-provided predetermined manganese content limits.

In another embodiment of the present invention, the selected matrix material comprises less than about 1,500 wppm, more preferably less than about 300 wppm, and most preferably less than about 150 wppm vanadium and vanadium-containing species, based on the total weight of the matrix material. Preferably, the low vanadium content matrix material is selected from the group consisting of: kaolin, halloysite, kaolinite, dickite, nacrite, montmorillonite, hectorite, saponite and laponite. Typically, these exemplary low vanadium content matrix materials have varying vanadium content levels, depending on the particular matrix material sample. For example, one kaolin clay from one sample may have a higher vanadium content than a kaolin clay from another sample, e.g., obtained from another region. As a result, to ensure that a particular clay sample contains a sufficiently low vanadium content to be suitable as a matrix material, the clay sample preferably is analyzed through well-known techniques, described in more detail below, to determine whether the clay sample's vanadium content is below any of the above-provided predetermined vanadium content limits.

In another embodiment of the present invention, the selected matrix material comprises less than about 1,500 wppm, more preferably less than about 100 wppm, and most preferably less than about 5 wppm cobalt and cobalt-containing species, based on the total weight of the matrix material. Preferably, the low cobalt content matrix material is selected from the group consisting of: kaolin, halloysite, kaolinite, dickite, nacrite, montmorillonite, hectorite, saponite and laponite. Typically, these exemplary low cobalt content matrix materials have varying cobalt content levels, depending on the particular matrix material sample. For example, one kaolin clay from one sample may have a higher cobalt content than a kaolin clay from another sample, e.g., obtained from another region. As a result, to ensure that a particular clay sample contains a sufficiently low cobalt content to be suitable as a matrix material, the clay sample preferably is analyzed through well-known techniques, described in more detail below, to determine whether the clay sample's cobalt content is below any of the above-provided predetermined cobalt content limits.

As indicated above, some kaolin clays, which have the low metal contents claimed herein, are particularly preferred matrix materials. Kaolin is a naturally-found usually white soft plastic clay composed primarily of well-ordered kaolinite mineral [Al2Si2O5(OH)4] with minor amounts of quartz, feldspar, and sheet silicate minerals such as mica, illite, smectite and chlorite. Geologically, kaolin deposits are typically characterized as being primary or secondary kaolin. Primary kaolin is formed through the alteration, or kaolinization, of in situ minerals of feldspar and other aluminum silicates to kaolinite. Secondary kaolin is laid down as sediments, usually in fresh water, far from where the kaolin originated. According to the present invention, either primary or secondary clays may be used as matrix materials.

As indicated above, some kaolins (as well as other clays) have metal contents that are too high to be satisfactorily used as a matrix material in a molecular sieve catalyst composition. For example, Ivrindi (Balikesir-Turkey) alunitic kaolin may have an Fe2O3 content of 2.77 weight percent or higher, based on the total weight of the kaolin sample. Kaolin mined around St. Austell, Cornwall, UK may have an Fe2O3 content of up to 1.2 weight percent or more, based on the total weight of the kaolin sample. Additionally, almost all kaolin deposits show very inhomogeneous structures. That is, kaolin compositions (and corresponding metal contents) vary widely throughout a given deposit and from region to region. Thus, analytical analysis may be necessary to determine whether the particular clay sample has a sufficiently low metal content for use as a matrix material according to the present invention. The analytical analysis preferably is by ICP/AES analysis, atomic adsorption spectroscopy (AAS) and/or x-ray fluorescence (XRF).

An exemplary non-limiting list of kaolin clays that may be used as a matrix material according to the present invention includes 6-Tile, EPK (Edgar Plastic Kaolin from Edgar, Fla.), Dixie, McNamee, Ione (California), Kyanite, Mullite, Kaopaque-20, Velvacast, Grolleg (United Kingdom), Georgia and Florida clays. Any of these kaolins, or others, may be implemented as the matrix material of the molecular sieve catalyst composition of present invention, so long as the particular sample has the low metal contents claimed herein.

VI. Forming Molecular Sieve Catalyst Compositions

As indicated above, once the molecular sieve is synthesized, depending on the requirements of the particular conversion process, the molecular sieve is then formulated into a molecular sieve catalyst composition as described in more detail below. The molecular sieves synthesized above are made or formulated into molecular sieve catalyst compositions by combining the synthesized molecular sieve(s) with a matrix material and optionally a binder to form a formulation composition. This formulation composition is formed into useful shape and sized particles by well-known techniques such as spray drying, pelletizing, extrusion, and the like, spray drying being the most preferred. It is also preferred that after spray drying for example that the formulation composition is then calcined.

In one embodiment, the weight ratio of the binder to the molecular sieve is in the range of from about 0.1 to 0.5, preferably in the range of from 0.1 to less than 0.5, more preferably in the range of from 0.11 to 0.48, even more preferably from 0.12 to about 0.45, yet even more preferably from 0.13 to less than 0.45, and most preferably in the range of from 0.15 to about 0.4. In another embodiment, the weight ratio of the binder to the molecular sieve is in the range of from 0.11 to 0.45, preferably in the range of from about 0.12 to less than 0.40, more preferably in the range of from 0.15 to about 0.35, and most preferably in the range of from 0.2 to about 0.3. All values between these ranges are included in this patent specification.

In another embodiment, the molecular sieve catalyst composition or formulated molecular sieve catalyst composition has a micropore surface area (MSA) measured in m2/g-molecular sieve that is about 70 percent, preferably about 75 percent, more preferably 80 percent, even more preferably 85 percent, and most preferably about 90 percent of the MSA of the molecular sieve itself. The MSA of the molecular sieve catalyst composition is the total MSA of the composition divided by the fraction of the molecular sieve contained in the molecular sieve catalyst composition.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrate. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrate, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol AL20DW, available from Nyacol Nano Technologies, Inc., Ashland, Mass.

In one embodiment, the binder, the synthesized molecular sieve and the matrix material are combined in the presence of a liquid slurrying medium such as water to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid.

Upon combining the synthesized molecular sieve and the matrix material, optionally with a binder, in a liquid to form a slurry, mixing, preferably rigorous mixing is needed to produce a substantially homogeneous mixture containing the synthesized molecular sieve. Non-limiting examples of suitable liquid slurrying mediums include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The liquid containing synthesized molecular sieve and matrix material, and the optional binder, are in the same or different liquid, and are combined in any order, together, simultaneously, sequentially, or a combination thereof. In the preferred embodiment, the same liquid, preferably water is used.

The molecular sieve catalyst composition in a preferred embodiment is made by preparing a slurry containing a molecular sieve, a matrix material and a binder. The solids content of the preferred slurry includes from about 20% to about 50% by weight molecular sieve, preferably from about 30% to about 48% by weight molecular sieve, more preferably from about 40% to about 48% by weight molecular sieve, from about 5% to about 20%, preferably from about 8% to about 15%, by weight of binder, and about 30% to about 80%, preferably about 40% to about 60%, by weight matrix material.

In another most preferred embodiment, the solids content in a slurry comprising a molecular sieve, a binder, and optionally a matrix material, and a liquid medium is in the range of from about 20 weight percent to about 80 weight percent, more preferably in the range of from 30 weight percent to about 70 weight percent, even more preferably in the range of from 35 weight percent to 60 weight percent, still even more preferably from about 36 weight percent to about 50 weight percent, yet even more preferably in the range of from 37 weight percent to about 45 weight percent, and most preferably in the range of from 38 weight percent to about 45 weight percent.

As the slurry is mixed, the solids in the slurry aggregate preferably to a point where the slurry contains solid molecular sieve catalyst composition particles. It is preferable that these particles are small and have a uniform size distribution such that the d90 diameter of these particles is less than 20 µm, more preferably less than 15 µm, and most preferably less than 10 µm. The d90 for purposes of this patent application and appended claims means that 90 percent by volume of the particles in the slurry have a particle diameter lower than the d90 value. For the purposes of this definition, the particle size distribution used to define the d90 is measured using well known laser scattering techniques using a Microtrac Model S3000 particle size analyzer from Microtrac, Inc. (Largo, Fla.). In one embodiment, the slurry of the invention contains at least 90 percent by volume of the molecular sieve catalyst composition particles comprising the molecular sieve, optionally binder, and matrix material, have a diameter of less than 20 µm, preferably less than 15 µm, and most preferably less than 10 µm.

In one preferred embodiment the slurry comprises a liquid portion and solid portion, wherein the solid portion comprises solid particles, the solid particles comprising a molecular sieve, a binder and a matrix material; wherein the slurry contains in the range of from about 30 weight percent to about 50 weight percent solid particles, preferably from about 35 weight percent to 45 weight percent, and at least 90 percent of the solid particles having a diameter less than 20 µm, preferably less than 10 µm.

In one embodiment, the slurry of the synthesized molecular sieve, binder and matrix material is mixed or milled to achieve a sufficiently uniform slurry of sub-particles of the molecular sieve catalyst composition to form a formulation composition that is then fed to a forming unit that produces the molecular sieve catalyst composition or formulated molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, any one or a combination of the slurries described above, more particularly a slurry of the synthesized molecular sieve, matrix material, and binder, is co-fed to the spray dryer with a drying gas with an average inlet temperature ranging from 200° C. to 550° C., and a combined outlet temperature ranging from 100° C. to about 225° C. In an embodiment, the average diameter of the spray dried formed catalyst composition is from about 40 µm to about 300 µm, preferably from about 50 µm to about 250 µm, more preferably from about 50 µm to about 200 µm, and most preferably from about 65 µm to about 90 µm.

During spray drying, the slurry is passed through a nozzle distributing the slurry into small droplets, resembling an aerosol spray, and into a drying chamber. Atomization is achieved by forcing the slurry through a single nozzle or multiple nozzles with a pressure drop in the range of from 100 psig to 2000 psig (690 kPag to 13790 kPag), preferably from 100 psig to 1000 psig (690 kPag to 6895 kPag). In another embodiment, the slurry is co-fed through a single nozzle or multiple nozzles along with an atomization fluid such as air, steam, flue gas, or any other suitable gas with a pressure drop preferably in the range of from 1 psig to 150 psig (6.9 kPag to 1034 kPag).

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve composition in a powder or a microsphere form.

Generally, the size of the microspheres is controlled to some extent by the solids content of the slurry. However, control of the size of the catalyst composition and its spherical characteristics are controllable by varying the slurry feed properties and conditions of atomization. In one embodiment, the catalyst composition has a d50 particle size from about 20 to about 200 microns. The dx particle size for purposes of this patent application and appended claims means that x percent by volume of a specified plurality of particles have a particle diameter no greater than the dx value. For the purposes of this definition, the particle size distribution (PSD) used to define the dx value is measured using well known laser scattering techniques using a Microtrac Model S3000 particle size analyzer from Microtrac, Inc. (Largo, Fla.). The "median particle diameter" is the d50 value for a specified plurality of particles. "Particle diameter" as used herein means the diameter of a specified spherical particle or the equivalent diameter of non-spherical particles as measured by laser scattering using a Microtrac Model S3000 particles size analyzer.

Thus, in one embodiment, the invention is directed to a process for forming a molecular sieve catalyst composition in which a matrix material is selected containing less than 10,000 wppm, more preferably less than about 7,000 wppm, and most preferably less than about 4,000 wppm iron and iron-containing species, based on the total weight of the matrix material. Preferably, the low iron content matrix material is selected from the group consisting of: kaolin, halloysite, kaolinite, dickite, nacrite, hectorite and laponite. A slurry is formed containing the matrix material, molecular sieves, a slurrying medium and optionally binder. The slurry is then dried to produce the molecular sieve catalyst composition.

In another embodiment, the invention is directed to a process for forming a molecular sieve catalyst composition in which a matrix material is selected containing less than 15,000 wppm, more preferably less than about 10,000 wppm, and most preferably less than about 5,000 wppm titanium and titanium-containing species, based on the total weight of the matrix material. Preferably, the low titanium content matrix material is selected from the group consisting of: kaolin, halloysite, kaolinite, dickite, nacrite, montmorillonite, saponite, hectorite and laponite. A slurry is formed containing the matrix material, molecular sieves, a slurrying medium and optionally binder. The slurry is then dried to produce the molecular sieve catalyst composition.

In another embodiment, the invention is directed to a process for forming a molecular sieve catalyst composition in which a matrix material is selected containing less than 1,500 wppm, more preferably less than about 300 wppm, and most preferably less than about 150 wppm nickel and nickel-containing species, based on the total weight of the matrix material. Preferably, the low nickel content matrix material is selected from the group consisting of: kaolin, halloysite, kaolinite, dickite, nacrite, montmorillonite, hectorite, saponite and laponite. A slurry is formed containing the matrix material, molecular sieves, a slurrying medium and optionally binder. The slurry is then dried to produce the molecular sieve catalyst composition.

In another embodiment, the invention is directed to a process for forming a molecular sieve catalyst composition in which a matrix material is selected containing less than 1,500 wppm, more preferably less than about 300 wppm, and most preferably less than about 150 wppm manganese and manganese-containing species, based on the total weight of the matrix material. Preferably, the low manganese content matrix material is selected from the group consisting of: kaolin, halloysite, kaolinite, dickite, nacrite, montmorillonite, hectorite, saponite and laponite. A slurry is formed containing the matrix material, molecular sieves, a slurrying medium and optionally binder. The slurry is then dried to produce the molecular sieve catalyst composition.

In another embodiment, the invention is directed to a process for forming a molecular sieve catalyst composition in which a matrix material is selected containing less than 1,500 wppm, more preferably less than about 300 wppm, and most preferably less than about 150 wppm vanadium and vanadium-containing species, based on the total weight of the matrix material. Preferably, the low vanadium content matrix material is selected from the group consisting of: kaolin, halloysite, kaolinite, dickite, nacrite, montmorillonite, hectorite, saponite and laponite. A slurry is formed containing the matrix material, molecular sieves, a slurrying medium and optionally binder. The slurry is then dried to produce the molecular sieve catalyst composition.

In another embodiment, the invention is directed to a process for forming a molecular sieve catalyst composition in which a matrix material is selected containing less than 1,500 wppm, more preferably less than about 100 wppm, and most preferably less than about 5 wppm cobalt and cobalt-containing species, based on the total weight of the matrix material. Preferably, the low cobalt content matrix material is selected from the group consisting of: kaolin, halloysite, kaolinite, dickite, nacrite, montmorillonite, hectorite, saponite and laponite. A slurry is formed containing the matrix material, molecular sieves, a slurrying medium and optionally binder. The slurry is then dried to produce the molecular sieve catalyst composition.

Other processes for forming a molecular sieve catalyst composition are described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, preferably from about 10% to about 90%, more preferably from about 10% to about 80%, even more preferably from about 20% to about 70%, and most preferably from about 25% to about 60% by weight of the molecular sieve based on the total weight of the molecular sieve catalyst composition.

Once the molecular sieve catalyst composition is formed in a substantially dry or dried state, to further harden and/or activate the formed catalyst composition, a heat treatment such as calcination, at an elevated temperature is preferably performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof. In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 20 hours. In a preferred embodiment, the molecular sieve catalyst composition is heated in nitrogen at a temperature of from about 600° C. to about 700° C. Heating is carried out for a period of time typically from 15 minutes to 15 hours, preferably from 30 minutes to about 10 hours, more preferably from about 30 minutes to about 5 hours.

In one embodiment, the attrition resistance of a molecular sieve catalyst composition is measured using an Attrition Rate Index (ARI), measured in weight percent catalyst composition attrited per hour. ARI is measured by adding 6.0 g of catalyst composition having a particles size ranging from 53 microns to 125 microns to a hardened steel attrition cup. Approximately 23,700 cc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent the catalyst composition that has broken apart through attrition. The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in weight percent per hour (wt. %/hr). ARI is represented by the formula: ARI=C/(B+C)/D multiplied by 100%, wherein B is weight of catalyst composition left in the cup after the attrition test, C is the weight of collected fine catalyst particles after the first hour of attrition treatment, and D is the duration of treatment in hours after the first hour attrition treatment.

In one embodiment, the molecular sieve catalyst composition or formulated molecular sieve catalyst composition has an ARI less than 15 weight percent per hour, preferably less than 10 weight percent per hour, more preferably less than 5 weight percent per hour, and even more preferably less than 2 weight percent per hour, and most preferably less than 1 weight percent per hour. In one embodiment, the molecular sieve catalyst composition or formulated molecular sieve catalyst composition has an ARI in the range of from 0 weight percent per hour to less than 5 weight percent per hour, more preferably from about 0.05 weight percent per hour to less than 3 weight percent per hour, and most preferably from about 0.01 weight percent per hour to less than 2 weight percent per hour.

In one preferred embodiment of the invention, the molecular sieve catalyst composition or formulated molecular sieve catalyst composition comprises a synthesized molecular sieve in an amount of from 20 weight percent to 60 weight percent, a binder in an amount of from 5 to 50 weight percent, and a matrix material in an amount of from 0 to 78 weight percent based on the total weight of the catalyst composition, upon calcination, and the catalyst composition having weight ratio of binder to sieve of from 0.1 to less than 0.5. In addition, the catalyst composition of this embodiment has an MSA on a contained sieve basis of the molecular sieve by itself from 450 m2/g-molecular sieve to 550 m2/g-molecular sieve, and/or an ARI less than 2 weight percent per hour.

In other preferred embodiments, the formulated catalyst composition, as a whole, has a low metal content. In these embodiments, the molecular sieve and the binder in addition to the matrix material are specifically selected for their low metal content. In order to formulate such low metal content catalyst compositions, the weight ratios of the molecular sieve, matrix mater, and optional binder optionally are selected in order to obtain a formulated catalyst composition having the desired low metal content. Thus, a catalyst composition according to this embodiment of the present invention may contain a matrix material having a relatively high metal content, e.g., more than 10,000 wppm iron and iron-containing species, although the formulated molecular sieve catalyst composition has a low metal content because the catalyst composition has a relatively high molecular sieve to matrix material weight ratio. In this embodiment, however, it is important that the molecular sieve and optional binder have low metal contents.

For example, in one embodiment, the invention is directed to a catalyst composition including a molecular sieve, a matrix material, and optionally a binder. The catalyst composition contains less than about 10,000 wppm iron and iron-containing species, based on the total weight of the catalyst composition. Optionally, the catalyst composition contains less than about 7,000 wppm or less than about 4,000 wppm iron and iron-containing species, based on the total weight of the catalyst composition.

In another embodiment, the invention is directed to a catalyst composition including a molecular sieve, a matrix material, and optionally a binder. The catalyst composition contains less than about 15,000 wppm titanium and titanium-containing species, based on the total weight of the catalyst composition. Optionally, the catalyst composition contains less than about 10,000 wppm or less than about 5,000 wppm titanium and titanium-containing species, based on the total weight of the catalyst composition.

In another embodiment, the invention is directed to a catalyst composition including a molecular sieve, a matrix material, and optionally binder. The catalyst composition contains less than about 1,500 wppm nickel and nickel-containing species, based on the total weight of the catalyst composition. Optionally, the catalyst composition contains less than about 300 wppm or less than about 150 wppm nickel and nickel-containing species, based on the total weight of the catalyst composition.

In another embodiment, the invention is directed to a catalyst composition including a molecular sieve, a matrix material, and optionally binder. The catalyst composition contains less than about 1,500 wppm cobalt and cobalt-containing species, based on the total weight of the catalyst composition. Optionally, the catalyst composition contains less than about 100 wppm or less than about 5 wppm cobalt and cobalt-containing species, based on the total weight of the catalyst composition.

In another embodiment, the invention is directed to a catalyst composition including a molecular sieve, a matrix material, and optionally binder. The catalyst composition contains less than about 1,500 wppm manganese and manganese-containing species, based on the total weight of the catalyst composition. Optionally, the catalyst composition contains less than about 300 wppm or less than about 150 wppm manganese and manganese-containing species, based on the total weight of the catalyst composition.

In another embodiment, the invention is directed to a catalyst composition including a molecular sieve, a matrix material, and optionally binder. The catalyst composition contains less than about 1,500 wppm vanadium and vanadium-containing species, based on the total weight of the catalyst composition. Optionally, the catalyst composition contains less than about 300 wppm or less than about 150 wppm vanadium and vanadium-containing species, based on the total weight of the catalyst composition. The invention is also direct to processes for formulating such low metal content catalyst compositions, as described above.

The invention is also directed to a process for converting an oxygenate in an oxygenate-containing feedstock to light olefins in the presence of the above-described low metal content molecular sieve catalyst compositions. The process includes providing an oxygenate in an oxygenate-containing feedstock, and contacting the oxygenate with a molecular sieve catalyst composition in a reaction zone under conditions effective to convert at least a portion of the oxygenate to light olefins and oxygenate byproducts, which are yielded from the reaction zone in a reaction effluent. Optionally, the reaction effluent contains less than about 10 weight percent, less than about 5 weight percent, less than about 3 weight percent, or less than about 1 weight percent oxygenate byproducts, based on the total weight of the reaction effluent.

VII. Processes For Using Low Metal Content Molecular Sieve Catalyst Compositions The molecular sieve catalyst compositions or formulated molecular sieve catalyst compositions described above are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve catalyst compositions described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene. Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition of the invention into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking. The most preferred process is generally referred to as gas-to-olefins (GTO) or alternatively, methanol-to-olefins (MTO). In a GTO process, typically natural gas is converted into a synthesis gas that is converted into an oxygenated feedstock, preferably containing methanol, where the oxygenated feedstock is converted in the presence of a molecular sieve catalyst composition into one or more olefin(s), preferably ethylene and/or propylene. In a MTO process, typically an oxygenated feedstock, most preferably a methanol containing feedstock, is converted in the presence of a molecular sieve catalyst composition thereof into one or more olefin(s), preferably and predominantly, ethylene and/or propylene, often referred to as light olefin(s).

In one embodiment, the present invention provides a process for producing light olefins while minimizing the formation of metal catalyzed side reaction byproducts formed in the reaction system. The process includes providing an oxygenate in an oxygenate-containing feedstock. The oxygenate contacts a molecular sieve catalyst composition under conditions effective to convert at least a portion of the oxygenate to light olefins and oxygenate byproducts in a reaction effluent, wherein the reaction effluent contains less than about 10 weight percent, more preferably less than about 5 weight percent, more preferably less than about 3 weight percent, or more preferably less than about 1 weight percent oxygenate byproducts, based on the total weight of the reaction effluent. For purposes of the present specification and the appended claims, an "oxygenate byproduct" is a molecule, other than dimethyl ether, that is formed in a reaction process and which contains at least one oxygen atom, at least one carbon atom and at least two hydrogen atoms. A non-limiting list of exemplary oxygenate byproducts includes: formaldehyde, ethanal, propanal, butanal, pentanal and higher aldehydes; acetone, butanone, pentanone, hexanone and higher ketones; methyl ethyl ether, diethyl ether, ethyl propyl ether and higher ethers; unsaturated species thereof, e.g., crotonaldehyde; formic acid, acetic acid, propionic acid, butanoic acid and higher carboxylic acids.

In one embodiment, the molecular sieve catalyst composition contains a matrix material, which comprises less than 10,000 wppm, more preferably less than about 7,000 wppm, and most preferably less than about 4,000 wppm of iron and iron-containing species, based on the total weight of the matrix material. In another embodiment, the molecular sieve catalyst composition contains a matrix material, which comprises less than 15,000 wppm, more preferably less than about 10,000 wppm and most preferably less than about 5,000 wppm of titanium and titanium-containing species, based on the total weight of the matrix material. In another embodiment, the molecular sieve catalyst composition contains a matrix material, which comprises less than 1,500 wppm, more preferably less than about 300 wppm and most preferably less than about 150 wppm of nickel and nickel-containing species, based on the total weight of the matrix material. In another embodiment, the molecular sieve catalyst composition contains a matrix material, which comprises less than 1,500 wppm, more preferably less than about 300 wppm and most preferably less than about 150 wppm of manganese and manganese-containing species, based on the total weight of the matrix material. In another embodiment, the molecular sieve catalyst composition contains a matrix material, which comprises less than 1,500 wppm, more preferably less than about 300 wppm and most preferably less than about 150 wppm of vanadium and vanadium-containing species, based on the total weight of the matrix material. In another embodiment, the molecular sieve catalyst composition contains a matrix material, which comprises less than 1,500 wppm, more preferably less than about 100 wppm and most preferably less than about 5 wppm of cobalt and cobalt-containing species, based on the total weight of the matrix material. Optionally, the molecular sieve catalyst composition contains a matrix material selected from the group consisting of: rare earth metals, non-active metal oxides including zirconia, magnesia, thoria, beryllia, quartz, silica, or sols, silica-magnesia, silica-zirconia, silica-alumina, silica-alumina-thoria, synthetic clays, montmorillonite, kaolinite, halloysite, dickite, nacrite, anauxite, laponite, and synthetic mica montmorillonites.

In one embodiment of the process for converting a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent. In another embodiment of the process for conversion of one or more oxygenates to one or more olefin(s), the amount of ethylene and/or propylene produced based on the total weight of hydrocarbon product produced is greater than 65 weight percent, preferably greater than 70 weight percent, more preferably greater than 75 weight percent, and most preferably greater than 78 weight percent.

In another embodiment of the process for conversion of one or more oxygenates to one or more olefin(s), the amount ethylene produced in weight percent based on the total weight of hydrocarbon product produced, is greater than 30 weight percent, more preferably greater than 35 weight percent, and most preferably greater than 40 weight percent. In yet another embodiment of the process for conversion of one or more oxygenates to one or more olefin(s), the amount of propylene produced in weight percent based on the total weight of hydrocarbon product produced is greater than 20 weight percent, preferably greater than 25 weight percent, more preferably greater than 30 weight percent, and most preferably greater than 35 weight percent.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water for example, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, and most preferably from about 5 to about 25.

In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and Fluidization Engineering, D. Kunii and O. Levenspiel, Robert E. Krieger Publishing Company, New York, N.Y, 1977, which are all herein fully incorporated by reference. The preferred reactor type are riser reactors generally described in Riser Reactor, Fluidization and Fluid-Particle Systems, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564, 613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar or the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 hr-1 to about 20,000 hr-1 based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr-1 to about 5000 hr-1, preferably from about 2 hr-1 to about 3000 hr-1, more preferably from about 5 hr-1 to about 1500 hr-1, and most preferably from about 10 hr-1 to about 1000 hr-1. In one preferred embodiment, the WHSV is greater than 20 hr-1, preferably the WHSV for conversion of a feedstock containing methanol and dimethyl ether is in the range of from about 20 hr-1 to about 300 hr-1.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 hr-1 and a Temperature Corrected Normalized Methane Selectivity (TCNMS) of less than 0.016, preferably less than or equal to 0.01. See for example U.S. Pat. No. 5,952,538, which is herein fully incorporated by reference. In another embodiment of the processes for converting an oxygenate such as methanol to one or more olefin(s) using a molecular sieve catalyst composition, the WHSV is from 0.01 hr-1 to about 100 hr-1, at a temperature of from about 350° C. to 550° C., and silica to Me2O3 (Me is a Group IIIA or VIII element from the Periodic Table of Elements) molar ratio of from 300 to 2500. See for example EP-0 642 485 B1, which is herein fully incorporated by reference. Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, O3, SO3, N2O, NO, NO2, N2O5, air, air diluted with nitrogen or carbon dioxide, oxygen and water (U.S. Pat. No.6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa). The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference. In yet another embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system. In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference. Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, by controlling the flow of the regenerated molecular sieve catalyst composition or cooled regenerated molecular sieve catalyst composition from the regeneration system to the reactor system, the optimum level of coke on the molecular sieve catalyst composition in the reaction zone is maintained. There are many techniques for controlling the flow of a molecular sieve catalyst composition described in Michael Louge, Experimental Techniques, Circulating Fluidized Beds, Grace, Avidan and Knowlton, eds., Blackie, 1997 (336-337), which is herein incorporated by reference. In another embodiment, the optimum level of coke on the molecular sieve catalyst composition in the reaction zone is maintained by controlling the flow rate of oxygen containing gas flowing to the regenerator, a partial regeneration. Coke levels on the molecular sieve catalyst composition is measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and/or regenerated molecular sieve catalyst composition and/or cooled regenerated molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated and fresh molecular sieve catalyst composition that have varying levels of carbon and carbon-like deposits, e.g., coke. The measured level of these deposits, specifically coke, represents an average of the levels on individual molecular sieve catalyst composition particles.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like. Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. Nos. 5,960,643 (secondary rich ethylene stream), 5,019,143, 5,452,581 and 5,082,481 (membrane separations), 5,672,197 (pressure dependent adsorbents), 6,069,288 (hydrogen removal), 5,904,880 (recovered methanol to hydrogen and carbon dioxide in one step), 5,927,063 (recovered methanol to gas turbine power plant), and 6,121,504 (direct product quench), 6,121,503 (high purity olefins without superfractionation), and 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants. Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in Kirk-Othmer Encyclopedia of Chemical Technology, 4th Edition, Volume 9, John Wiley & Sons, 1996, pages 249-271 and 894-899, which is herein incorporated by reference. Purification systems are also described in for example, U.S. Pat. Nos. 6,271,428 (purification of a diolefin hydrocarbon stream), 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

In one embodiment, the effluent gas withdrawn from the reactor is passed through a recovery system producing one or more hydrocarbon containing stream(s), in particular, a three or more carbon atom (C3+) hydrocarbon containing stream. In this embodiment, the C3+ hydrocarbon containing stream is passed through a first fractionation zone producing a crude C3 hydrocarbon and a C4+ hydrocarbon containing stream, the C4+ hydrocarbon containing stream is passed through a second fractionation zone producing a crude C4 hydrocarbon and a C5+ hydrocarbon containing stream. The four or more carbon hydrocarbons include butenes such as butene-1 and butene-2, butadienes, saturated butanes, and isobutanes.

The effluent gas removed from a conversion process, particularly a MTO process, typically has a minor amount of hydrocarbons having 4 or more carbon atoms. The amount of hydrocarbons having 4 or more carbon atoms is typically in an amount less than 20 weight percent, preferably less than 10 weight percent, more preferably less than 5 weight percent, and most preferably less than 2 weight percent, based on the total weight of the effluent gas withdrawn from a MTO process, excluding water. In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water.

Suitable well known reaction systems as part of the recovery system primarily take lower value products and convert them to higher value products. For example, the C4 hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel. Non-limiting examples of reaction systems include U.S. Pat. Nos. 5,955,640 (converting a four carbon product into butene-1), U.S. Pat. No. 4,774,375 (isobutane and butene-2 oligomerized to an alkylate gasoline), 6,049,017 (dimerization of n-butylene), 4,287,369 and 5,763,678 (carbonylation or hydroformulation of higher olefins with carbon dioxide and hydrogen making carbonyl compounds), 4,542,252 (multistage adiabatic process), 5,634,354 (olefin-hydrogen recovery), and Cosyns, J. et al., Process for Upgrading C3, C4 and C5 Olefinic Streams, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a single carbon number olefin in an amount greater than 80 percent, preferably greater than 90 weight percent, more preferably greater than 95 weight percent, and most preferably no less than about 99 weight percent, based on the total weight of the olefin. In one embodiment, high purity prime olefin(s) are produced in the process of the invention at rate of greater than 5 kg per day, preferably greater than 10 kg per day, more preferably greater than 20 kg per day, and most preferably greater than 50 kg per day. In another embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. Nos. 6,121,503 (making plastic with an olefin product having a paraffin to olefin weight ratio less than or equal to 0.05), 6,187,983 (electromagnetic energy to reaction system), PCT WO 99/18055 publishes Apr. 15, 1999 (heavy hydrocarbon in effluent gas fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas. Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol. The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference. In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

EXAMPLE I

Formulating a Low Metal Content Molecular Sieve Catalyst Composition

In order to provide a better understanding of the present invention, the following experimental example is offered. In this example, a molecular sieve catalyst composition having a low-metal content matrix material was synthesized. In the experiment, a SAPO-34 molecular sieve catalyst composition, designated catalyst composition "A", was formulated following U.S. Pat. No. 6,440,894, the entirety of which is incorporated herein by reference. The silicon to aluminum atomic ratio of the as-synthesized SAPO-34 molecular sieve used to form the catalyst composition was determined to be 0.068 based on Inductively Coupled Plasma (ICP) spectroscopy analysis.

The matrix material used was specifically selected for its low metal content. Specifically, the matrix material selected was a kaolin clay sample containing less than 7,000 wppm iron (specifically, 5,400 wppm iron) and iron-containing species, less than 5,000 wppm titanium, less than 150 wppm Nickel and less than 5 wppm cobalt, based on the total weight of the matrix material. A slurry was formed containing the matrix material, SAPO-34 molecular sieve, a binder, and a slurrying medium. ICP analysis of the dissolved molecular sieve catalyst composition indicated that the catalyst composition contained 0.28 weight percent (2800 wppm) iron, less than 95.5 wppm nickel, 3248 wppm titanium and less than 5 wppm chromium, based on the total weight of the catalyst composition. An ICP spectrometer from TJA Solutions (IRIS Advantage) was used in obtaining the elemental analysis data reported in this specification. Lastly, the slurry was dried to produce the molecular sieve catalyst composition. The formulated catalyst composition had the following overall composition: 40 weight percent molecular sieve, 12 weight percent ACH (aluminum chlorhydrol) binder and with the rest (48 weight percent) being the kaolin clay matrix material, based on the total weight of the formulated catalyst composition. Methanol was reacted over the formulated catalyst composition, as discussed in Example II, below. The composition of the resulting product was analyzed to determine catalyst lifetime and the concentration of metal catalyzed side reaction byproducts found in the reaction effluent. The selectivity of methanol to various products in the presence of catalyst composition A is reflected in Table I, below.

EXAMPLE II

Comparing the Low Metal Content Molecular Sieve Catalyst Composition with Various Metal-Loaded Molecular Sieve Catalyst Compositions In an effort to better understand the effects that various metals have on MTO reaction systems, and particularly metals commonly found in MTO catalyst compositions, an experiment was conducted to determine whether various metals typically found in formulated molecular sieve catalyst compositions play a role in the formation of side reaction byproducts in an MTO reaction system, and if so, which metals most readily catalyze the formation of side reaction byproducts. The metals analyzed are commonly found in catalyst composition matrix materials.

Specifically, samples of catalyst composition "A" from Example I, above, which contained molecular sieve, binder and matrix material, were loaded with iron, nickel, titanium and chromium, respectively, through wet impregnation. Methanol was reacted over these loaded catalyst compositions as well as a control sample (catalyst composition A) in separate trial runs, and the composition of the resulting product was analyzed to determine whether the loaded catalyst compositions exacerbated the formation of metal catalyzed side reaction byproducts and if these metals have an effect on catalyst lifetime.

Wet impregnation was used for loading iron, nickel, chromium and titanium into respective samples of catalyst composition A. Fe(III)acetylacetonate, Ni(acetylacetonate)2, Cr(acetylacetonate)3 and Ti(IV)isopropoxide were used in the preparation of loaded catalyst samples Fe/A, Ni/A, Cr/A and Ti/A, respectively. In a typical preparation of catalyst composition Fe/A having 2.0 weight percent iron, 0.53 g of Fe(III)acetylacetonate was dissolved in 8 ml of acetone. The solution was added dropwise to 4.0 g of calcined molecular sieve catalyst composition A. The wet mixture was dried in a vacuum oven at 50° C. for 0.5 hour to remove the acetone. The dried solid was then calcined at 650° C. in air for 3 hours to form Fe/A. Similar procedures were followed in preparing Ni/A, Cr/A and Ti/A. The concentration of iron, nickel, titanium and chromium in each metal-loaded catalyst composition was measured by elemental analyses performed by Galbraith Lab to be 2.48 weight percent, 1.01 weight percent, 3.16 weight percent, and 0.84 weight percent, respectively, based on the total weight of the metal-loaded catalyst composition.

Experiments were then performed to determine the reactivity and light olefin selectivity of converting methanol in a micro flow reactor to light olefins over respective catalyst compositions Fe/A, Ni/A, Cr/A, Ti/A, and catalyst composition A (low-metal content) as well as on the coked versions of these catalysts. The temperature rise observed in the experiments was 5° C. or less. Typically, 95 mg of control catalyst composition A and each of the metal-loaded catalyst compositions, respectively, were mixed with 1 g of 100-mm siliconcarbide. The mixture was loaded into a microflow reactor, which was formed of 0.25 inch siliconsteel tubing. The reactor temperature was increased to 475° C. while the catalyst was under helium flow at 46 ml/min and was held at this temperature for about 30 to 40 minutes for temperature stabilization. Methanol was provided at a flow rate through reactor of about 80 ml/min at 475° C., 25 psig (172 kPag) and 100 WHSV. The reactor effluent formed was sampled in a multi-loop sampling valve to obtain the gas phase selectivity data.

A mixture of 10 ml/min of O2 and 10 ml/min of helium was flowed through the reactor for catalyst regeneration while the reactor temperature was increased from 475° C. to 550° C. A portion of the regeneration gas stream was sent into a nickel-containing methanator, which converted CO and CO2 in the effluent stream into methane in the presence of an excess amount of H2. The concentration of methane was then quantified by a FID detector. The amount of coke on the removed sieve was then measured by comparing the integrated peak area from the FID detector with that of a calibration standard.

The collected effluent samples were analyzed by on-line gas chromatography (Hewlett Packard 6890) equipped with a flame ionization detector. The chromatographic column used was a Low-ox column (Varian, cat. No. CP 8587, 10 m×0.53 mm).

The weighed averages (selectivities) of the effluent samples were calculated based on the following formula, (x1)(y1)+(x2−x1)(y2)+(x3−x2)(y2+y3)/2+(x4−x3)(y3+y4)/2+..., where xi and yi are yield and g methanol fed/g sieve, respectively. Catalyst Lifetime (g/g catalyst) reported is methanol that was cumulatively converted. Note that both the lifetime and WHSV were reported based on the weight of the sieve. Methanol converted at less than about 10 weight percent conversion was not included in the calculations.

Coke selectivities were calculated based on the FID measurement of the end-of-run coke (EOR) and the catalyst lifetime, i.e., Coke selectivity, weight percent=EOR coke (g coke/g sieve)/{lifetime (g methanol/g sieve)*14/32 (g CH2/g methanol)}* 100.

The selectivity of methanol conversion to the various products: C1 (methane)+C2 (ethane and ethylene), C3 (propane and propylene), C4 (butanes, butylene and butadiene), and the oxygenates ethyl ether, acetaldehyde, propanal, acetone, butanone, and pentanones, were determined through gas chromatography. The results for coked catalyst compositions are provided in Table I, below. The data provided in each of the columns of Table I (except catalyst lifetime, which is recorded in g/g catalyst) are weight percentages, based on the total weight of the effluent produced.

TABLE I

Catalyst Lifetime and Selectivity of Methanol to Oxygenates and Hydrocarbon Compounds Over Coked Metal-Loaded Catalysts

| Catalyst | C1 + C2 | C3 | C4 | Total Oxygenates[1] | Coke | C1 + C2 + C3 | Catalyst Lifetime |
|---|---|---|---|---|---|---|---|
| A | 38.13 | 39.15 | 19.14 | 0.90 | 2.68 | 77.28 | 18.44 |
| Fe/A | 37.76 | 38.45 | 18.73 | 1.17 | 3.91 | 76.20 | 13.40 |
| Ni/A | 39.85 | 37.39 | 16.84 | 1.08 | 4.84 | 77.24 | 10.04 |
| Cr/A | 38.00 | 39.51 | 19.23 | 0.85 | 2.42 | 77.51 | 20.48 |
| Ti/A | 39.08 | 37.21 | 18.29 | 1.05 | 4.38 | 76.29 | 12.58 |

[1]"Total Oxygenates" includes all oxygenate-containing species except methanol and DME.

The data provided above in Table I indicates that iron, nickel and titanium increase selectivity for metal catalyzed side reaction byproducts. Iron, nickel and titanium also significantly shorten catalyst lifetime and increase coke selectivity. For these reasons, iron, nickel and titanium and potentially other metals should be viewed as MTO catalyst poisons. Chromium, however, did not have a significant effect on the catalyst lifetime or selectivity. Each of these metals is typically present, often in high concentrations, in matrix materials that are implemented in forming formulated catalyst compositions.

While the present invention has been described and illustrated by reference to particular embodiments, those of ordinary skill in the art will appreciate that the invention lends itself to variations not necessarily illustrated herein. For example, it is contemplated that the molecular sieve catalyst composition is useful in the inter-conversion of olefin(s), oxygenate to gasoline conversions reactions, maleic anhydride, phthalic anhydride and acrylonitrile formulation, vapor phase methanol synthesis, and various Fischer Tropsch reactions. It is further contemplated that a plug flow, fixed bed or fluidized bed process are used in combination, particularly in different reaction zones within a single or multiple reactor system. It is also contemplated the molecular sieve catalyst compositions described herein are useful as absorbents, adsorbents, gas separators, detergents, water purifiers, and other various uses such as agriculture and horticulture. It is additionally contemplated that the molecular sieve catalyst compositions include one or more other molecular sieves in combination. For this reason, then, reference should be made solely to the appended claims for purposes of determining the true scope of the present invention.

We claim:

1. A process for producing light olefins, the process comprising the steps of:
   contacting an oxygenate with a molecular sieve catalyst composition and converting at least a portion of the oxygenate to a reaction product comprising light olefins and less than about 10 weight percent oxygenate byproducts, based on the total weight of the reaction product,
   wherein the molecular sieve catalyst composition contains a matrix material, the matrix material containing at least one of (i) less than 10,000 wppm of iron and iron-containing species, (ii) less than 15,000 wppm of titanium and titanium-containing species, (iii) less than 1,500 wppm of nickel and nickel-containing species, (iv) less than 1,500 wppm of cobalt and cobalt-containing species, (v) less than 1,500 wppm of manganese and manganese-containing species, and (vi) less than 1,500 wppm of vanadium and vanadium-containing species, based on the total weight of the matrix material.

2. The process of claim 1, wherein the reaction product comprises less than about 5 weight percent oxygenate byproducts, based on the total weight of the reaction effluent.

3. The process of claim 2, wherein the reaction product comprises less than about 3 weight percent oxygenate byproducts, based on the total weight of the reaction effluent.

4. The process of claim 3, wherein the reaction product comprises less than about 1 weight percent oxygenate byproducts, based on the total weight of the reaction effluent.

5. The process of claim 1, wherein the molecular sieve catalyst composition contains a matrix material, the matrix material containing at least one of (i) less than 7,000 wppm of iron and iron-containing species, (ii) less than 10,000 wppm of titanium and titanium-containing species, (iii) less than 300 wppm of nickel and nickel-containing species, (iv) less than 100 wppm of cobalt and cobalt-containing species, (v) less than 300 wppm of manganese and manganese-containing species, and (vi) less than 300 wppm of vanadium and vanadium-containing species, based on the total weight of the matrix material.

6. The process of claim 5, wherein the molecular sieve catalyst composition contains a matrix material, the matrix material containing at least one of (i) less than 4,000 wppm of iron and iron-containing species, (ii) less than 5,000 wppm of titanium and titanium-containing species, (iii) less than 150 wppm of nickel and nickel-containing species, (iv) less than 5 wppm of cobalt and cobalt-containing species, (v) less than 150 wppm of manganese and manganese-containing species, and (vi) less than 150 wppm of vanadium and vanadium-containing species, based on the total weight of the matrix material.

7. The process of claim 1, wherein the molecular sieve catalyst composition contains a matrix material selected from the group consisting of: rare earth metals, non-active metal oxides including zirconia, magnesia, thoria, beryllia, quartz, silica, or sols, silica-magnesia, silica-zirconia, silica-alumina, silica-alumina-thoria, synthetic clays, montmorillonite, kaolinite, halloysite, dickite, nacrite, anauxite, laponite, and synthetic mica montmorillonites.

8. The process of claim 1, wherein the molecular sieve catalyst composition contains a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof intergrown forms thereof and mixtures thereof.

9. The process of claim 8, wherein the molecular sieve is selected from the group consisting of SAPO-34, AEI/CHA intergrowths, the metal containing forms thereof, and mixtures thereof.

10. The process of claim 1, wherein the molecular sieve catalyst composition comprises (i) less than about 10,000 wppm of iron and iron-containing species, (ii) less than about 15,000 wppm of titanium and titanium-containing species, (iii) less than about 1,500 wppm of nickel and nickel-containing species, (iv) less than about 1,500 wppm of cobalt and cobalt-containing species, (v) less than about 1,500 wppm of manganese and manganese-containing species, and (vi) less than about 1,500 wppm of vanadium and vanadium-containing species, based on the total weight of the molecular sieve catalyst composition.

11. The process of claim 10, wherein the molecular sieve catalyst composition comprises (i) less than 7,000 wppm of iron and iron-containing species, (ii) less than 10,000 wppm of titanium and titanium-containing species, (iii) less than 300 wppm of nickel and nickel-containing species, (iv) less than 100 wppm of cobalt and cobalt-containing species, (v) less than 300 wppm of manganese and manganese-containing species, and (vi) less than 300 wppm of vanadium and vanadium-containing species, based on the total weight of the molecular sieve catalyst composition.

12. The process of claim 11, wherein the molecular sieve catalyst composition comprises (i) less than 4,000 wppm of iron and iron-containing species, (ii) less than 5,000 wppm of titanium and titanium-containing species, (iii) less than 150 wppm of nickel and nickel-containing species, (iv) less than 5 wppm of cobalt and cobalt-containing species, (v) less than 150 wppm of manganese and manganese-containing species, and (vi) less than 150 wppm of vanadium and vanadium-containing species, based on the total weight of the molecular sieve catalyst composition.

13. The process of claim 1, further comprising:
   contacting water in a synthsis gas production zone with a gaseous hydrocarbon feedstock comprising methane and/or ethane to make a synthesis gas comprising hydrogen and carbon monoxide,
   contacting the synthesis gas with a catalyst under conditions effective to produce the oxygenate, and polymerizing the light olefins.

14. The process of claim 13 further comprising purifying the light olefins before the polymerizing.

15. The process of claim 14, wherein the light olefins comprise ethylene and propylene and the purifying comprises removing from the reaction product one or more of water, alcohols, carboxylic acids, ethers, carbon oxides, hydrogen sulfide, carbonyl sulfides, mercaptans, ammonia, arsine, phosphine, chlorides, hydrogen, acetylene, methyl acetylene, propadiene, butadiene, and butyne.

16. The process of claim 15, wherein the light olefins comprise ethylene and/or propylene.

17. The process of claim 13 further comprising conducting at least one polymer away from the process.

18. The process of claim 17, wherein the polymer is at least one of linear low density polyethylene, elastomers, plastomers, high density polyethylene, low density polyethylene, polypropylene, and polypropylene copolymers comprising at least one of atactic polypropylene, isotactic polypropylene, syndiotactic polypropylene, and propylene random, block or impact copolymers.

19. The process of claim 13 further comprising separating and conducting away from the process at least one of aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

20. The process of claim 13, wherein the feedstock is produced from one or more of organic material, natural gas, petroleum liquids, and/or carbonaceous materials including coal, recycled plastic, and municipal waste.

21. The process of claim 13, wherein the feedstock is natural gas.

22. The process of claim 1 further comprising separating a C4+ hydrocarbon from the reaction product and conducting the C4+ hydrocarbon to a reaction system in order to make one or more of alcohols having 8 to 13 carbon atoms, methyl-t-butylether, butene-1, butene-2, alkylate gasoline, dimerized n-butylene, carbonyl compounds, and dimerized or oligomerized propylene, butylene and pentylene.

23. The process of claim 1 further comprising:

contacting water in a synthesis gas production zone with a gaseous hydrocarbon feedstock comprising methane and/or ethane obtained from natural gas to make a synthesis gas comprising hydrogen and carbon monoxide, contacting the synthesis gas with a catalyst to produce an impure oxygenate comprising crude methanol, purifying the crude methanol to make the oxygenate, purifying the reaction product to recover the light olefins, and polymerizing the light olefins to make at least a polyolefin.

* * * * *